US006679898B1

(12) United States Patent
Chuck

(10) Patent No.: US 6,679,898 B1
(45) Date of Patent: Jan. 20, 2004

(54) DEVICES AND METHODS FOR HARVESTING LIMBAL STEM CELLS

(75) Inventor: Roy S. Chuck, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 3 days.

(21) Appl. No.: 09/965,124

(22) Filed: Sep. 27, 2001

Related U.S. Application Data

(60) Provisional application No. 60/236,045, filed on Sep. 27, 2000.

(51) Int. Cl.[7] .................................................. A61F 9/00
(52) U.S. Cl. ...................................................... 606/166
(58) Field of Search .......................... 606/166; 604/521, 604/299; 623/4.1, 5.11, 5.12, 5.16, 6.11, 6.14, 6.64

(56) References Cited

U.S. PATENT DOCUMENTS

| | | | | |
|---|---|---|---|---|
| 5,980,543 A | * | 11/1999 | Carriazo et al. | 606/166 |
| 6,132,446 A | * | 10/2000 | Hellenkamp et al. | 606/166 |
| 6,302,896 B1 | * | 10/2001 | Carriazo et al. | 493/385 |
| 6,312,439 B1 | * | 11/2001 | Gordon | 347/37 |
| 6,332,890 B1 | * | 12/2001 | Ortega et al. | 606/166 |
| 6,447,528 B2 | * | 9/2002 | Paraschac | 606/190 |
| 6,506,198 B1 | * | 1/2003 | Amano | 606/166 |

OTHER PUBLICATIONS http://elliseye.com/chapter_6.html: A general discussion of Lasik surgery and related information.*
Basti, Surendra, M.D., et al., Current Status of Limbal Conjunctival Autograft, Current Opinion in Ophthalmology, 2000, 11:224–232.
Beebe, David C. and Masters, Barry R., Cell Lineage and the Differentiation of Corneal Epithelial Cells, Investigative Ophthalmology & Visual Science, Aug. 1996, vol. 37, No. 9, pp 1815–1825.
Behrens, M.D., Ashley, Shah, M.D., Samir B., Li, M.D., Li, Coe, M.D., Mary A., Liaw,Liaw, M.S., Leacky L.H., Sweet, M.T., Paula M., McDonnell, M.D., Peter J., and Chuck, M.D., Ph.D., Roy S., Evaluation of a Microkeratome–Based Limbal Harvester Device for Limbal Stem Cell Transplantation, Corena, 2002, vol. 21, No. 1, pp 51–55.
Chuck, MD, Roy S., Behrens, MD, Ashley and McDonnell, MD, Peter J., Microkeratome–Based Limgbal Harvester for Limbal Stem Cell Transplantation: Preliminary Studies, American Journal of Ophthalomology, Mar. 2001, pp 377–378.
Chen, James J.Y. and Tseng, Scheffer C.G., Corneal Epithelial Wound Healing in Partial Limbal Deficiency, Investigative Ophthalmology & Visual Science, vol. 31, No. 7, Jul. 1990.

(List continued on next page.)

Primary Examiner—Julian W. Woo
Assistant Examiner—Paul Roberts
(74) Attorney, Agent, or Firm—Robert D. Buyan; Stout, Uxa, Buyan & Mullins, LLP

(57) ABSTRACT

A system, apparatus and method for harvesting from the eye of a mammilian (e.g., cadaveric) donor a disc-shaped graft or lenticle consisting of corneal tissue and a quantity of scleral or pericorneal tissue wherein limbal stem cells are located. This graft or lenticle is then transplanted onto the eye of a human or veterinary patient to treat a disorder caused by the absence or deficiency of limbal stem cells in the patient's eye. The system of the present invention comprises a) an eye-contacting ring and cutter guide apparatus and b) a cutter apparatus. The eye-contacting ring and cutter guide apparatus is initially placed in contact with the donor eye such that a portion of the cornea and adjacent scleral or pericorneal tissue containing limbal stem cells protrudes upwardly through the center of the ring. The cutter is then engaged with guide member(s) formed on the ring and the cutter is advanced, severing the protruding cornea and stem-cell-containing pericorneal tissue. In this manner the desired lenticle is obtained for subsequent transplantation.

7 Claims, 4 Drawing Sheets

OTHER PUBLICATIONS

Coster, Douglas J., Aggrawal, Rajesh K., WIlliams, Keryn A., Surgical Management of Ocular Surface Disorders Using Conjunctival and Stem Cell Allografts, Br F Ophthalmol, 1995, vol. 79, pp 977–982.

Cotsarelis, George, Cheng, Shih–Zen, DOng, Gang, Sun, Tung–Tien and Lavker, Robert M., Existensce of Slow–Cycling Limbal Epithelial Basal Cells That Can Be Preferentially Stimulated to Proliferate: Implications of Epithelial Stem Cells, Cell, vol. 57, pp. 201–209, Apr. 1989.

Davanger, M. and Evensen, A., Role of the Pericorneal Papillary Structure in Renewal of Corneal Epithelium, Makerere University College, May 1970.

Dua, Harminder S., Azuara–Blanco, Augusto, Allo–Limbal Transplantation in Patients with Limbal Stem Cell Dificiency, Br F Ophthalmol, 1999, vol. 83, pp 414–419.

Dua, M.D., Harminder S. and Forrester, M.D., John V., The Corneoscleral Limbus in Human Corneal Epithelial Wound Healing, American Journal of Ophthalmology, vol. 110, pp 646–656, Dec. 1990.

Solomon, A, et al., Long–Term Outcome of Keratolimbal Allograft With or Without Penetrating Keratoplasty for Total Limbal Stem Cell Dificiency, Ophthalmology, vol. 109, No. 6, pp 1159–1166, Jun. 2002.

Dua, MD, Harminder S., et al., Limbal Stem Cells of the Corneal Epithelium, Survey of Ophthalmology, vol. 44, No. 5, pp 415–425, Mar. 2000.

Kenyon, MD, et al., Limbal Autograft Transplantation for Ocular Surface Disorders, Ophthalmology, vol. 96, No. 5, pp 709–723, May 1989.

Lehrer, Michael S., et al., Strategies of Epithelial Repair: Modulation of Stem Cell and Transit Amplifying Cell Prolifera tion, Journal of Cell Science, vol. 111, pp2867–2875, 1998.

Shimazaki, MD, Jun, The Evolution of Iamellerar Kertoplasty, Ophthalmology, vol. 11, pp 217–223, 2000.

Shimazaki, Jun, et al., Evidence of Long–Term Tsurvival of Donor–Derived Cells After Limbal Allograft Transplantation, Investigative Ophthalmology & Visual Science, vol. 40, pp. 1664–1668, Jul. 1999.

Terry, M.D., Mark A., The Evloution of Lamellar Grafting Techniques Over Twenty–Five Years, Cornea, vol. 19, No. 5, pp 611–616, 2000.

Tsai, MD, Ray Jui–Fang, Reconstruction of Damaged Corneas by Transplantation of Autologous Limbal Epithelial Cells, The New England Journal of Medicine, vol. 343, No. 2, pp. 86–93, Jul. 2000.

Tsai, M.D., Ray Jui–Fang, et al., Human Allograft Limbal Transplantation for Corneal Surface Reconstruction, Cornea, vol. 13, No. 5, pp 389–400, 1994.

Tsubota, M.D., Kazuo, et al., Treatment of Severe Ocular–Surface Disorders with Corneal Epithelial Stem–Cell Transplantation, The New England Journal of Medicine, vol. 340, No. 22, pp 1697–1703, Jun. 1999.

Tungsiripat, M.D., Tulaya, et al., Viability of Limbal Corneal Epithelium After Anterior Lamellar Harvesting Using a Microkeratome, pp. 1–26.

Sarayba, M.D., Melvin A., A Portable Microkeratome–Based Anterior Corneal Surface Harvesting Device, Cornea, vol. 21, No. , pp 589–591—2002.

Chuck, Roy S., et al., 193 nm Excimer Laser–Induced Fluorescence from Fluoroquinolone–Treated Rabbit Corneas, pp. 1–25, 2002.

Thoft, Richard, The X, Y, Z Hypothesis of Corneal Epithelial Maintenance, Investigative Ophthalmology & Visual Science, Oct. 1983.

* cited by examiner

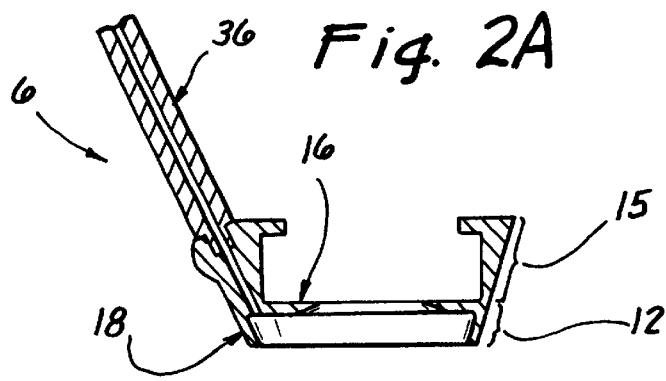
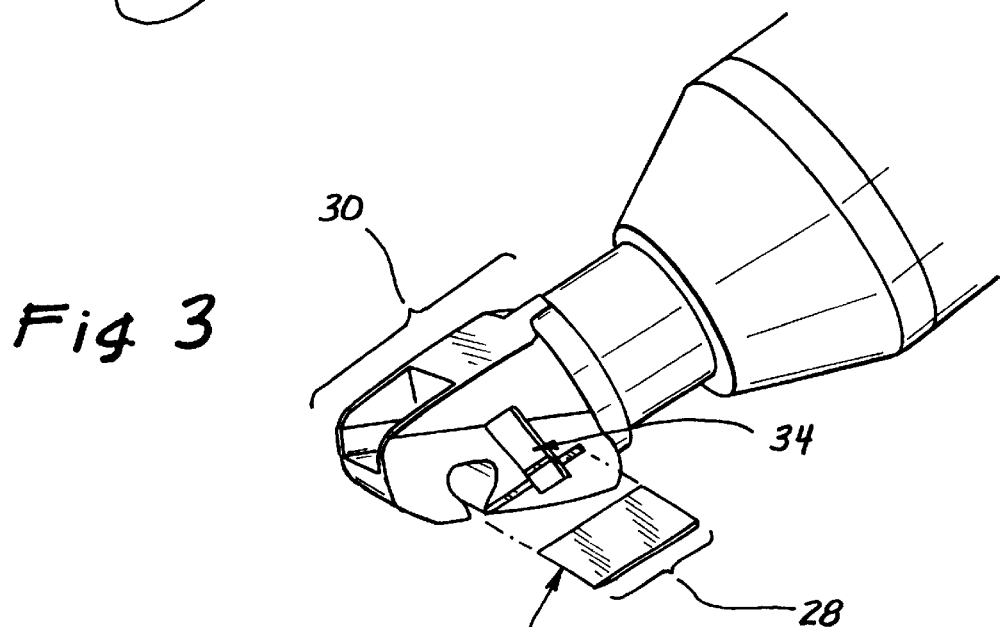
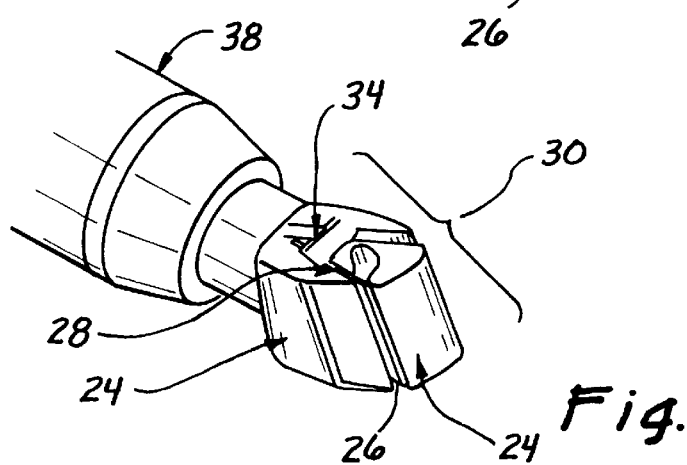

DEVICES AND METHODS FOR HARVESTING LIMBAL STEM CELLS

RELATED APPLICATION

This patent application claims priority to U.S. Provisional Application No. 60/236,045 entitled "Method and Apparatus for Corneal Transplantation" filed on Sep. 27, 2000.

FIELD OF THE INVENTION

The present invention relates generally to medical devices and methods and more particularly to a device and method for harvesting a quantity of transplantable corneal tissue along with adjacent, stem-cell-containing scleral tissue.

BACKGROUND OF THE INVENTION

The anterior portion of the human eye normally contains corneal, limbal, and conjunctival epithelial tissue. Along with a film of tears, these tissues cover and protect the eye. The limbus is the marginal region of the cornea of the eye by which the cornea is continuous with the sclera. There is experimental and clinical evidence that limbal epithelial stem cells are located in the limbal area, presumably in the basal epithelium allowing the cells to be harvested as a lamellar eye tissue section. These dynamic cells maintain the corneal epithelial cell population and thus, the corneal surface integrity. Thus, the presence of functioning limbal stem cells is critical to the health and functioning of the eye. In the event the limbal stem cells become damaged or depleted, chronic inflammation, cloudy vision, and even blindness may result.

Damage or depletion to the limbal epithelial (stem) cells can result from a number of causes, including trauma, chemical or thermal burns, a disorder known as Stevens-Johnson syndrome, improper fitting or improper use of contact lenses, infections and/or scarring due to prior surgical procedures. In some cases, severe damage may lead to complete loss of the limbal epithelial cells.

In cases where only one eye is affected, the deficiency of limbal stem cells in the damaged eye may be treated by transplantation of a quantity of autologus limbal tissue harvested from the patient's own contralateral healthy eye. However, because of the large amount of limbal tissue must be taken, it is not always possible to harvest enough limbal tissue from the patient's good eye to complete the autologus transplant procedure in the bad eye. Also, the removal of tissue from the good eye can result in complications or visual changes in the good eye.

Another approach is to harvest limbal tissue (containing the limbal stem cells) from the eye of a cadaveric donor and to subsequently transplant those donor stem cells into the patient's eye. The harvesting of limbal stem cells from cadaveric donors has heretofore typically been carried out by first removing the ocular globe from the donor's body, then carefully removing a quantity of corneal tissue along with the scleral rim (the pericorneal scleral tissue) to obtain a generally disc shaped graft that includes the anterior cornea and adjacent limbus. This procedure has been performed by hand, and thus there is significant variability in the size and shape of the harvested graft.

The first studies proposing a pericorneal network responsible for the corneal epithelial cell maintenance were published three decades ago (Davanger M et al, 1971). Several authors have supported the hypothesis of a limbal stem cell system, based on the indirect evidence obtained from clinical experience and experimental work (Cotsarelis G et al, 1989; Lehrer M S et al, 1989; Chen J J et al, 1990; Dua H S et al, 1990; Dua H S et al, 2000). Epithelial cell behavior has also been extensively studied to evaluate the dynamics of its mitosis and migration (Thoft R A et al, 1983; Beebe D C et al, 1996). In cases of severe stem cell deficiency, surgical intervention is required. Limbal stem cell transplantation was first reported in 1989 by Kenyon and Tseng (Kenyon K R et al, 1989).

Results for the autologous transplantation of the limbal area in severe ocular surface disorders have been promising (Basti S et al, 2000; Tsai R J et al, 2000). In addition, allograft transplantation of these cells has been attempted, especially when a healthy donor tissue is not available in the contralateral eye (Tsai R J et al, 1994; Coster D J et al, 1995; Tsubota K et al, 1999; Dua H S et al, 1999). That is, the posterior two thirds of the cornea is manually removed, as well as the central 7.5 or 8 mm. Thus this annulus contains the outer 3 to 4 mm of limbal epithelium. Conversely, if this margin is too generous, then much more antigenic tissue is being transferred than is required for a successful epithelial stem cell graft. Most surgeons, however, will err on the conservative side, and transfer too much rather than too little tissue. Initial results for the autologous transplantation of the limbal area in severe ocular surface disorders have been promising (Basti S et al, 2000; Tsai R J et al, 2000). In addition, allograft transplantation of these cells has been attempted, especially when a healthy donor tissue is not available in the contralateral eye (Tsai R J et al, 1994; Coster D J et al, 1995; Tsubota K et al, 1999; Dua H S et al, 1999). With the development of new strategies for immunosupression and the refinements in screening for donor tissue compatibility, these allograft procedures for limbal stem cell transplantation have become more successful and thus been more common in the last few years (Terry M A, 2000; Shimazaki J et al, 2000; Shimazaki J et al, 1999; Tsai R J et al, 1994, Tsubota K, 1999).

The most troublesome technical concern with the transplantation procedure is the manual limbal tissue harvest. This is a time consuming process and certainly inaccurate, since the cut depth can only be visually estimated. In addition, the free-hand donor harvest of the limbal area is laborious, likely results in mechanical trauma and dehydration effects on vulnerable cell populations, and may be associated with poor preservation of the stem cells.

What is needed is a system to perform a superficial cut of the corneal-scleral surface to obtain a partial thickness lenticule containing a rim of sclera. This may ensure the presence of sufficient limbal area for 360° to obtain the stem cells required for a successful transplant.

SUMMARY OF THE INVENTION

The present invention provides a system for harvesting corneal tissue along with adjacent scleral tissue containing limbal stem cells. The system of the present invention generally comprises an eye-contacting guide apparatus in combination with a tissue cutting apparatus. The eye-contacting guide apparatus may comprise a ring member or other suitable device that is positionable an the anterior surface of an eye which will guide the tissue cutting apparatus so as to form a precisely positioned cut in the eye tissue, harvesting the corneal and adjacent scleral tissue in which the limbal stem cells are located.

In accordance with the invention there is provided a system and method for harvesting, from a mammalian eye, a transplantable graft consisting of a quantity of corneal tissue along with a quantity of pericorneal tissue (e.g., scleral tissue) wherein the limbal stem cells are located. Generally, the system of the present invention comprises two components, namely a) an eye-contacting ring and guide member and b) a cutter. The eye-contacting ring and guide member may comprise a ring member, having an upper surface and a lower surface, and a cutter guide attached to or formed on the ring member for guiding the cutter along a predetermined path above the ring member. The cutter may generally comprise a handpiece attached to a blade for cutting the corneal and adjacent scleral tissue. The ring member may be sized such that when its lower surface is placed in contact with the anterior aspect of the eye, a portion of the cornea and adjacent scleral tissue will protrude upwardly through the ring member above the ring member's upper surface and in relation to the cutter guide such that when the cutter is advanced along the cutter guide it will remove a disc shaped graft or "lenticule" consisting of corneal tissue along with the desired quantity of adjacent scleral tissue wherein limbal stem cells are contained.

Still further in accordance with the present invention, a device of the invention may include a blade oscillator for causing the blade to oscillate or move from side to side to enhance its ability to form a clean cut through the corneal and scleral tissue. In some embodiments the oscillator is pneumatic.

Still further in accordance with the present invention, the ring member may be secured to the eye. In one embodiment, the ring member is secured to the eye by a partial vacuum. The partial vacuum may be contained within an anular structure which is made up of two surfaces, an upper surface and a lower surface, of the ring member and the surface of the eye.

Still further in accordance with the present invention, the inner diameter of the ring member may be about 14 mm to about 30 mm or about 14 mm to about 24 mm or about 14 mm to about 18 mm or about 16 mm or 16 mm.

Still further in accordance with the present invention, the cutter may include a guide-engaging member, which engages and interacts with the guide (e.g., guide member(s), guide trace, mechanical linkage, magnets or any other suitable apparatus for holding and guiding the cutter) located on the eye-contacting ring and guide apparatus.

Still further in accordance with the present invention, the ring member may include a handle useable for holding and manipulating the eye-contacting ring and guide apparatus.

Still further in accordance with the present invention, there are provided methods for harvesting a graft or lenticule consisting of corneal tissue and a quantity of pericorneal tissue and/or scleral tissue wherein limbal stem cells are located. In these methods a portion of the eye-contacting ring and guide member, for example, a lower surface of the ring member, may be placed in contact with the anterior aspect of the donor eye such that the cornea and a portion of the pericornial sclera protrudes upwardly through the ring member. The cutter may be engaged with the cutter guide and the cutter advanced along the cutter guide such that the blade means severs a quantity of corneal tissue along with a quantity of pericorneal scleral tissue.

Any and all features described herein and combinations of such features are included within the scope of the invention provided that such features of any such combination are not mutually exclusive.

These and other aspects and advantages of the present invention are apparent in the following detailed description and claims.

BRIEF DESCRIPTION OF THE DRAWINGS

FIG. 2A shows a longitudinal sectional view through line 2A of FIG. 2.

FIG. 3 is a partial perspective view of a distal portion of the tissue cutter apparatus of the system of FIG. 1.

FIG. 3A shows a perspective view of the underside of the distal portion of the tissue cutter apparatus of FIG. 3.

DETAILED DESCRIPTION OF THE INVENTION

Figure 1:
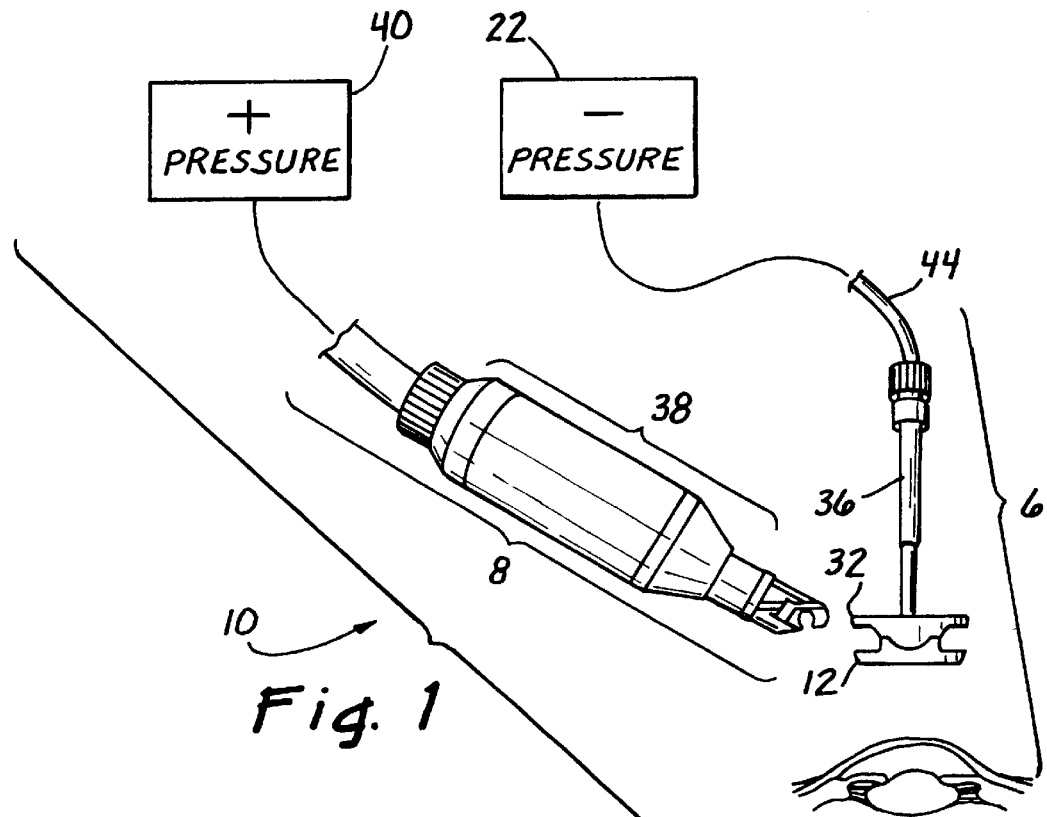
FIG. 1 is a perspective showing of a system of the present invention.
Figure 2:
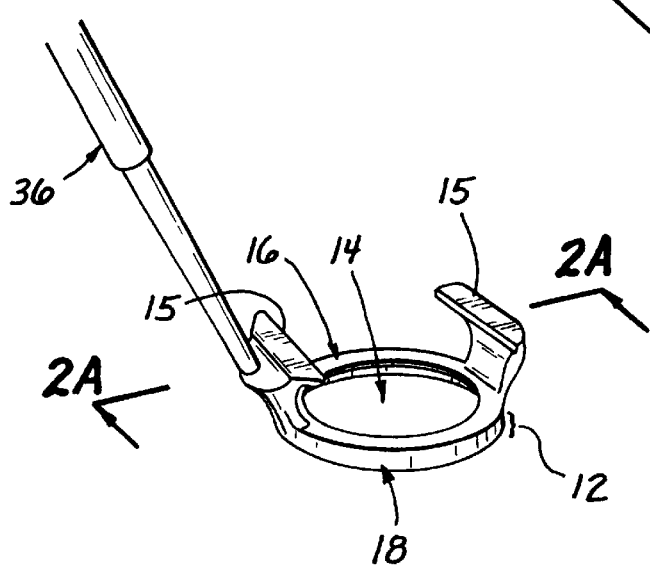
FIG. 2 is a perspective view of a portion of the eye-contacting guide apparatus of the system of FIG. 1.

The following detailed description and the drawings to which it refers are provided for the purpose of describing and illustrating certain examples and embodiments of the present invention.

In the accompany figures wherein an eye or portion of an eye is shown, certain anatomical structures of the eye are labeled as follows: L=lens; I=iris; C=cornea; LM=limbus and S=sclera.

The system 10 of the present invention generally comprises an ring and guide apparatus 6 and a cutter apparatus 8. In the embodiment shown in the figures, the ring and guide apparatus 6 comprises template ring 12 having an upper rim 16 and a lower rim 18, a cutter guide 15 and a gripping handle 36. The cutter apparatus 8 may include a blade 28, a blade carriage 30, a cutter guide 15, an applanation plate 24, a guide engaging means 34, and a maneuvering handle 38.

The template ring 12 is used to encircle the eye tissue to be harvested. The template ring 12 has a central opening 14 which is of a sufficient diameter to encompass the limbus LM of an eye when the template ring 12 is placed in contact with an eye.

Figure 4:
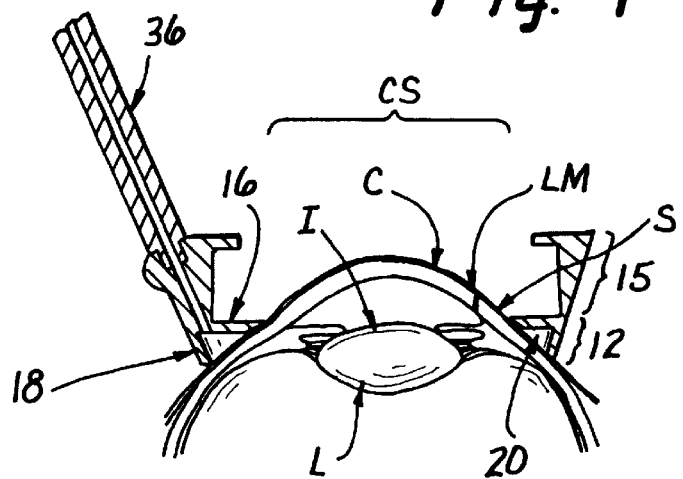
FIG. 4 shows a longitudinal sectional view of a portion of the eye-contacting guide apparatus of taken through line 2A—2A of FIG. 2.

A suction chamber or other suitable means may be used to secure the template ring 12 to the eye. For example, serrations or projections may be provided on the surface of the template ring 12, which comes in contact with the eye. In another example, a securing apparatus which is affixed to the template ring 12 may be attached to the head of the donor. Alternatively, temporary sutures or temporary, biologically compatible adhesive may be used to secure the template ring 12 in place. In another example, the template ring 12 may be held in place by pressure exerted by the operator of the device pressing down on the template ring 12 by use of a gripping handle 36. In one particularly useful embodiment of the invention, a partial vacuum is used to secure the template ring 12 to the eye. In this embodiment, the central opening 14 is defined in part by an upper rim 16 and a lower rim 18. The lower rim 18 is larger in diameter than the upper rim 16 in correspondence to the natural curvature of the anterior aspect of the eye. Thus, when seated upon the eye as shown in FIG. 4B, the upper and lower rims 16, 18 will each contact the eye thus forming an anular chamber 20. The template ring may have a gripping handle 36 attached. In one embodiment, the gripping handle 36 comprises a tube which is attached to the template ring 12 and is centered over a hole in the template ring 12. This hole leads to the anular opening that becomes the anular chamber 20 when the template ring 12 is placed in contact with an eye (FIG. 4). In one embodiment, the gripping handle 36 comprises a tube and a line 44 is attached to a vacuum source and to the gripping handle 36 at the end of the gripping handle 36 distal to the template ring 12. The vacuum source 22 is activated and pressure is transferred to the anular chamber 20 until a partial vacuum is achieved to seat the template ring 12 in place on the eye. The vacuum source 22 may be, for example, automatically powered, for example, electrically powered, or a manually powered pump. In one embodiment, the vacuum source is supplied by a hand-powered vacuum pump. The vacuum pressure employed may be sufficient to hold the template ring 12 in place on the eye while the blade carriage 30 is passed across the template ring. For example, a pressure of about 40 to about 400 cmHg may be use. In another example, a pressure of about 50 to about 70 cmHg may be used. Use of combinations of these means to secure the template ring 12 in place is within the scope of the present invention. For example, both a partial vacuum and operator pressure may be used to hold the template ring 12 in place.

Figure 5E:
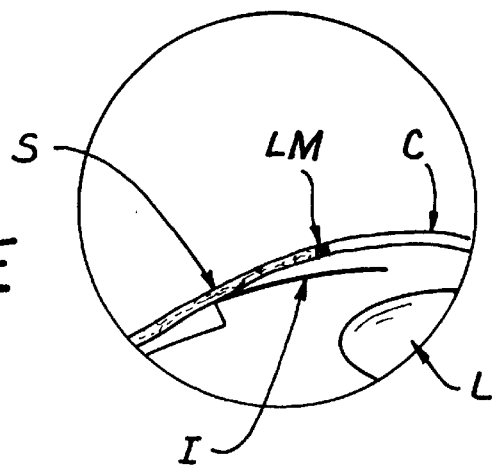
FIGS. 5A–5F are a schematic, step-by-step illustration of a procedure for harvesting corneal-scleral tissue from a cadaveric eye.
Figure 5F:
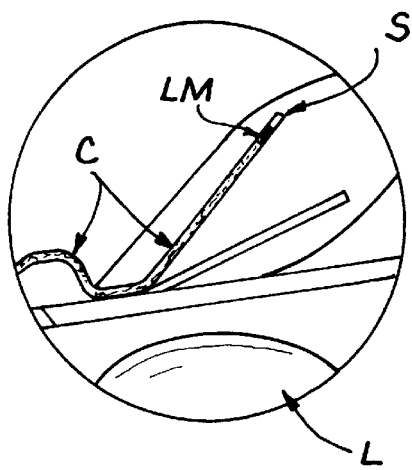
Figure 5A:
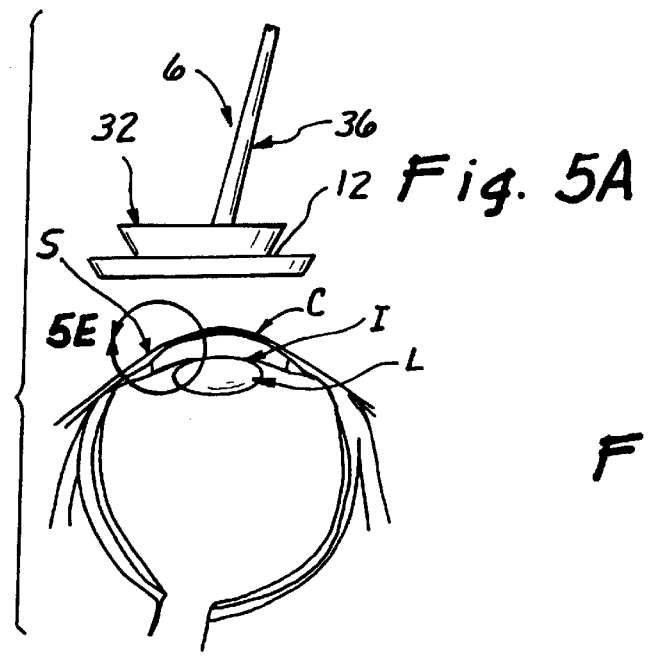
Figure 5B:
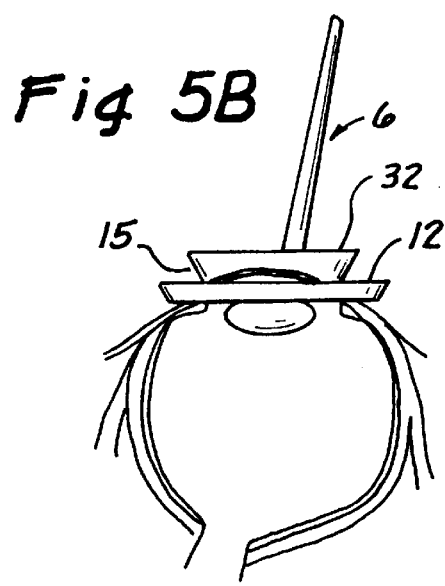
Figure 5C:
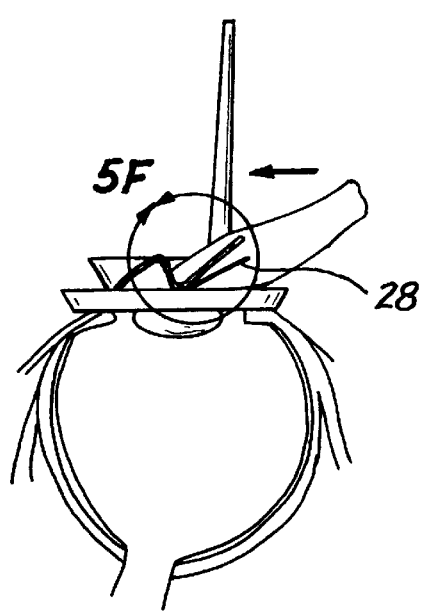

The bottom section of the blade carriage 30 includes an applanation plate 24, which functions to flatten the eye tissue to be harvested in advance of the blade 28 (FIG. 5C). The distance of the blade's cutting edge 26 to the applanation plate 24 may define the thickness of the eye tissue, for example, the corneal-scleral CS tissue to be harvested. The distance of the blade's cutting edge 26 to the applanation plate 24 of the blade carriage 30 may be from about 1.00 mm to about 0.01 mm. In one embodiment of the invention, the distance of the blade's cutting edge 26 to the applanation plate 24 is about 0.17 mm. In another embodiment, the distance of the blade's cutting edge 26 to the applanation plate 24 is about 0.2 mm. In a preferred embodiment, the distance of the blade's cutting edge 26 to the applanation plate 24 of the blade carriage 30 is a distance that optimizes the presence of basal epithelial cells of the limbal area in the harvested tissue.

A blade 28 is employed in the present invention and may be housed in a blade carriage 30. In one embodiment, a 16 mm wide blade is housed in a 16 mm blade carriage. The blade carriage 30 may be coupled with a power source that imparts a cutting motion to the blade 28. The power source may be electric, pneumatic or other. In one embodiment, a pneumatic power source is provided by pressurized gas 40, for example, pressurized nitrogen gas. The cutting motion supplied by the power source may be, for example, an oscillating motion. The oscillating motion may be supplied by, for example, a turbine. In one particularly useful embodiment of the present invention, a pressurized gas 40 driven turbine imparts an oscillating motion to a blade 28 which is housed in a blade carriage 30. In one embodiment, the pressurized gas 40 is pressurized nitrogen. In one embodiment, the action of the turbine may drive the blade 28 inside the blade carriage 30 at approximately 15,000 oscillations per minute. In one embodiment, he turbine is housed in a maneuvering handle of a blade carriage 30.

The blade carriage 30 may contain a guide engaging means 34. The guide engaging means 34 is used in combination with a cutter guide 15 which may be included on the template ring. The combination guide engaging means 34 and cutter guide 15 are designed to assist the blade carriage 30 in passing uniformly across the eye, for example, passing uniformly across the corneal-scleral CS tissue of the eye. When the blade carriage 30 is passed across the eye, the blade 28 comes in contact with and cuts away (harvests) eye tissue, for example, corneal-scleral CS tissue that protrudes above the central opening of the template ring 12 (FIG. 4).

In one embodiment, the guide engaging means 34 is located on two sides of the blade carriage 30 and corresponds to a cutter guide 15 included on the template ring12. The blade carriage 30 may be passed across the template ring 12 and the eye by an automated means, for example, by a motor driven means. In one embodiment of the invention, the blade carriage 30 has attached a maneuvering handle 38 and is manually passed across the eye tissue to be harvested by assistance from the maneuvering handle.

The present invention encompasses methods for using devices of the above description to harvest tissue of an eye. For example, the devices may be used to harvest sclera tissue, cornea tissue, pericorneal tissue and/or corneal-scleral tissue from an eye.

In one embodiment of the invention, an operator applies the template ring 12 to the surface of an eye. The template ring 12 may be centered on an eye and is wide enough to encompass the limbus LM of an eye. If the template ring 12 is centered on the eye, the operator may use the limbus LM as reference to do so. A gripping handle 36 may be attached to the template ring 12 which allows the operator to move and stabilize the template ring 12 using either the left hand or the right hand. In one embodiment, the template ring is secured in place by activation of a vacuum source 22. In one embodiment, the vacuum source is a manually operated, portable pump that is usable without electrical power which facilitates usage of the system 10 in locations where electrical power may be unavailable.

A microscope, for example, a surgical microscope, may be used in operation of the device. The microscope may be integral to the device or separate. The microscope is positioned so as to assist the operator in controlling the pass of the blade carriage 30 over the eye tissue to be harvested. For example, the microscope may be positioned to view a device of the invention from a point that is above the device when the device is in use.

An operator of the device may pass the blade carriage 30 over the seated template ring 12 and in doing so the applanation plate 24 and a blade 28 housed in the blade carriage 30 come in contact with eye tissue that is within the circular span of the template ring. In one embodiment, the blade carriage 30 is automatically passed across the template ring. In another embodiment, the blade carriage 30 is passed over the template ring 12 by manual assistance from the operator. In order for the operator to hold and control the blade carriage 30, a maneuvering handle 38 may be attached to the blade carriage 30. In one embodiment, a single operator may grasp a gripping handle 36 with one hand and may use the other hand to grasp the maneuvering handle 38 and pass the blade carriage 30 across the template ring 12 and eye tissue thereby cutting away and harvesting the eye tissue, for example, the corneal-scleral tissue CS (FIG. 5).

In one embodiment of the invention, a gripping handle 36 and a maneuvering handle 38 are oriented perpendicular to each other (FIG. 1). The blade carriage 30 may be passed, for example, in a left to right manner across the template ring 12 or in a right to left manner across the template ring 12.

The guide engaging means 34 and cutter guide 15 may be used in combination to assist the operator in controlling the pass of the blade carriage 30 over the template ring 12. When passing the blade carriage 30 over the template ring 12, a powered cutting means may be imparted to a blade 28 housed in the blade carriage 30. For example a blade oscillation driven by pressurized gas, for example, pressurized nitrogen gas may be used.

Figure 5D:
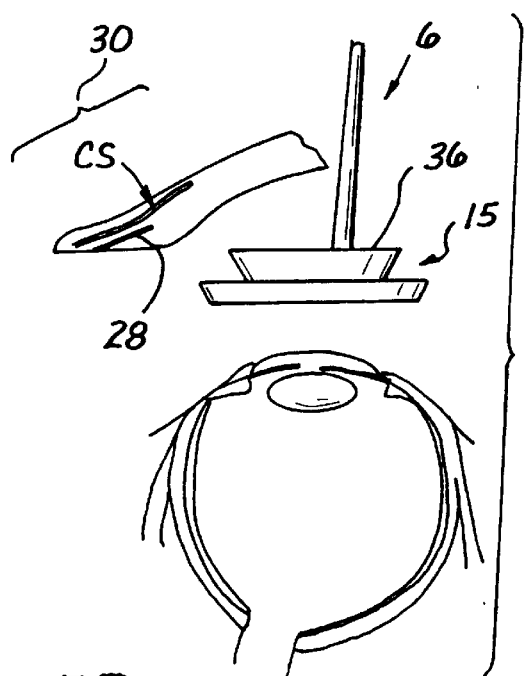

FIGS. 5A–5F depicts harvesting corneal-scleral tissue by a method of the present invention. The template ring 12 is first seated on the eye (FIGS. 5A–5B). The applanation plate 24 of the blade carriage 30 is contacted with the tissue of the eye and the contacted portion of the eye is flattened (FIG. 5C). The cutting edge of the blade 26, reaches below the applanation plate 24 and cuts the eye tissue as the blade carriage 30 is passed across the template ring 12 (FIG. 5C). In a preferred embodiment, the operator passes the blade carriage 30 across the template ring 12 in a single smooth even motion. In passing the blade carriage 30 completely across the template ring 12, a lamellar piece of corneal-scleral CS is cut and harvested from the eye (FIG. 5D).

EXAMPLE 1

Evaluation of Harvester Device for Corneal-Scleral Lenticule Harvest From Pig's Eyes The cutter 14 used in this example comprises a blade carriage 30 which houses a blade 28 coupled with a nitrogen gas driven turbine. The turbine action drives the blade 28 inside the blade carriage 30 at approximately 15,000 oscillations per minute. The blade carriage 30 is designed for a manual pass across the corneal-scleral CS region of an eye with guide engaging means 34 designed to fit into the cutter guide 15 on the template ring. This allows constant height and centration of the blade carriage 30 during the pass. The template ring 12 is connected to a vacuum pump 22. The central opening of the template ring 12 is a diameter of 16 mm, which encompasses the entire corneal-scleral CS surface of a donor globe.

Twenty-five fresh pig eyes were obtained from a local slaughterhouse and stored in saline for experimental use the same day. They were randomly assigned to two groups (170 vs. 200 um blade carriage). Each globe was inflated to an intraocular pressure of 15–25 mmHg with normal saline and placed in a globe holder. The epithelium was mechanically removed from all samples. The template ring 12 was centered on each cornea, and vacuum was achieved using the maximum pressure pulled by the hand pump (58–64 cmHg). The intraocular pressure was recorded while the globe was under this high vacuum (Modular One Pneumotonometer, Mentor O&O, Norwell, Mass.). The globe surface was then lubricated with balanced salt solution and a right to left pass with the microkeratome was performed under a surgical microscope (Ophthalmic 900S, Moeller-Wedel Microsurgical, Mason, Ohio).

To assess cut reproducibility the physical dimensions of the obtained lenticules were measured. Diameter measurements were performed by placing each sample onto a flat surface, digitally photographing them and analyzing with imaging software (Scion Image, Scion Corp., Frederick, Md.). The horizontal meridian corresponds to the direction of the blade carriage 30 pass.

All statistical analyses were performed using SPSS 10.00 (t Test for Independent Means). A P value of 0.05 was considered statistically significant. The obtained lenticules were fairly circular (horizontal vs. vertical diameters, P>0.2), with average diameters of 12.85±0.52 mm and 13.25±1.15 mm for the 170 and 200 um heads, respectively.

Variations in lenticule thickness were assessed by measuring each cap in the center and 4 quadrants in the mid-periphery (Ophthasonic A Scan-Pachometer III, Mentor O&O, Norwell, Mass.). The average central lenticule thickness obtained was 176.92±34.68 $\mu$m and 166.00±53.74 $\mu$m for the 170 and 200 um heads, respectively. Each lenticule obtained was fairly uniform in thickness, as no statistically significant variations were found upon comparing the 5 measurement points.

The manual vacuum pump was able to achieve an average suction pressure of 63.0±1.6 cmHg.

This portable device allows harvest of large and reasonably thick anterior corneal lenticules using porcine globes. Comparing the porcine with the human cornea, the porcine is significantly larger (16.16 mm×13.63 mm average porcine diameter vs. 12.6 mm×11.7 mm average human diameter) and flatter (37.74 D average porcine keratometry vs. 43 D average human keratometry). When applied to the human eye, the obtained lenticule contains the limbal stem cell region as well as the other anterior lamellar planes, as was shown in a previous study using an electric vacuum pump. This has been verified in preliminary studies using the manual vacuum pump (data not shown).

This system presents an economical and portable system for the harvest of transplantable corneal-scleral sections. Because the device uses no electricity and requires only a small compressed gas tank for power, multiple uses are possible. Besides being used by surgeons in the operating room, it could theoretically be used by eye bank technicians in the field, including in third world countries where cost, availability of electricity and portability are issues. The machine could either be used on whole globes at the eye bank, or directly on the intact eyes of the fresh cadaver. Moreover, after the human corneal surface containing the limbal stem cell region and an anterior corneal lenticule are taken, the posterior lamellar region containing the endothelial layer may be trephined and stored for endokeratoplasty. That is, very simply and on a large scale, three lamellar corneal grafts could be harvested from each human donor globe for eye bank storage and subsequent distribution for transplantation.

EXAMPLE 2

Evaluation of Limbal Harvester Device for Limbal Stem Cell Transplantation

Donor Tissue. Twenty six (26) fresh human donor globes not suitable for corneal transplantation were obtained received in a cool moist chamber from the eyebank. Those having central corneal thickness of ≧1020 $\mu$m, corneas with evident stromal or limbal scars, or a marked surface irregularity were excluded. Sixteen eyes were therefore included in the study. The eyes were divided in two groups to accommodate two different blade carriage 30 cut thicknesses (170 and 200 $\mu$m, n=8 each). Globes were randomly assigned to either group upon availability.

Mechanical Device. The system 10 of the present invention was Used to harvest disc shaped grafts from the globes. The cutter of a blade carriage 30 which houses a blade 28 coupled with a nitrogen gas driven turbine. The turbine action drives the blade 28 inside the blade carriage 30 at approximately 15,000 oscillations per minute. The blade carriage 30 is designed for a manual pass across the corneal-scleral CS region of an eye with guide engaging means 34 designed to fit into the cutter guide 15 on the template ring 12. This allows constant height and centration of the carriage during the pass. The template ring 12 is connected to a vacuum pump. The central opening 14 of the template ring 12 is a diameter of 16 mm, which encompasses the entire corneal-scleral CS surface of a donor globe.

Two different carriages were used: 170 and 200 um. This number represents the measured distance of the blade's cutting edge to the applanation plate built into the head.

A similar cut depth was expected, to ensure the presence of basal epithelial cells of the limbal area in the lenticule.

The blade carriage 30 houses a custom-made 16 mm stainless steel blade to match the width of the carriage.

Procedure. The globes were pressurized by inserting a 25-gauge needle connected to a bottle of saline through the optic nerve. Care was taken to maintain an intraocular pressure (IOP) within 15–25 mmHg. The IOP was measured prior application of the template ring 12 with a pneumatonometer (Modular One, Mentor O&O, Norwell, Mass.), and the bottle height set accordingly. The same operator performed the tissue harvesting on all eyes in a right to left hand translation to avoid bias related to hand dominance and experience. The template ring 12 was applied to the globe surface and centered, using the limbus as reference. The vacuum source was activated and manual pressure was transferred to the anular chamber 20 until adequate suction to hold the template ring 12 in place was achieved. A surgical microscope (Ophthalmic 900S, Moeller-Wedel Microsurgical, Mason, Ohio) was used to control the pass. Alcaine® eye drops (proparacaine 1%, Alcon, Ft. Worth, Tex.) were applied to the exposed corneal-scleral surface (to avoid saline), and the activated turbine with its blade carriage 30 was passed over the template ring 12 without stopping. The corneal-scleral CS lenticule was obtained under microscope visual control during the pass.

Lenticule Dimensions. To assess cut reproducibility, physical dimensions were measured. The lenticule thickness was measured in four quadrants and in the center using an ultrasound pachymeter (Ophthasonic A Scan-Pachometer III, Mentor O&O, Norwell, Mass.), using arbitrary orthogonal axes at the center of the cornea as a reference. Central epithelial removal of ~9 mm area was performed prior to tissue harvesting to avoid bias due to irregular post-mortem epithelial thickness. The thickness was recorded prior to and after the cut, and the lenticule thickness calculated by subtraction.

For lenticule diameter measurements, digital macrophotography (Olympus 3030, Tokyo, Japan) of the residual bed in the whole eye at high-resolution settings (2,500×1028 pixel) were taken. The images were downloaded to digital imaging software (Scion Image, Scion Corp., Frederick, Md.) and after calibration, horizontal and vertical meridian diameters were recorded.

Tissue Preservation, Histology and Scanning Electron Microscopy (SEM). To detect lenticule thickness changes after immersion in Optisol® (Bausch&Lomb Surgical, Irvine, Calif.), the lenticules were preserved in vials with the media for 4 days at 4° C. Thickness measurements were performed by placing the lenticules on a plastic dome of a known thickness. The domes were made from cut ends of Falcon test tubes. Calculations were made by subtraction, as previously described.

For histology, lenticules were fixed in 10% buffered paraformaldehyde, paraffin embedded and cut in 5 µm sections for hematoxilin-eosin staining. For SEM analysis, specimens were immersed in osmium tetroxide, dehydrated with graded alcohols and dried using increasing concentrations of hexamethyldisilazane. Samples were gold-sputtered and examined under a scanning electron microscope (Philips XL 30, Limeil-Brevannes, France).

Statistical Analysis. We used StatsDirect® 1.7.4 statistical software (CamCode, Ashwell, UK) for the analysis. Descriptive statistics (mean, standard deviation, minimum and maximum value) were performed for continuous variables. Comparisons between groups were performed using non-parametric tests (Mann-Whitney U for unpaired samples, Wilcoxon's signed ranks test for paired samples). A P-value $\leq 0.05$ was considered statistically significant.

Results. The demographic and morphometric data obtained from the donor globes is shown in Table 1.

The instrument was easy to use as no problems were encountered during the procedure. The total procedure time was approximately 30 s, of which 15 s are related to the pass of the blade carriage 30 across the template ring.

TABLE 1

Data Collected from Donor Globes

| Head Size | Donor Age (years) | Gender (Female/Male) | Time after Death (hr) | Central Corneal Thickness (µm) | Preoperative IOP (mmHg) |
|---|---|---|---|---|---|
| 170 | 72.3 (11.7)* [54–85]† | 6/2 | 135.0 (60.1)* [66–192]† | 900 (85)* [792–1019]† | 17.1 (2.6)* [13.6–21.8]† |
| 200 | 81.4 (15.4)* [56–97]† | 0/10 | 143.9 (63.9)* [40–216]† | 894 (148)* [632–998]† | 18.3 (4.6)* [12.7–26.0] |

*mean (SD); †[range]

No central buttonholes were observed in this series.

The results of lenticule dimensions are shown in Table 2. Comparing lenticule sizes using the two blade carriages, the horizontal (in the same direction of the pass) diameter was significantly larger using the 170 blade carriage (P=0.028). However, in the vertical diameter the measurements were somewhat similar (P=0.093). Regarding thickness, similar thickness values were obtained using both heads either at the center (P=0.720), at the beginning of the pass (P=0.943), at the end of the pass (P=0.243), superiorly (P=0.075), or inferiorly (P=0.180). Moreover, no significant differences between or within groups were observed comparing the central thickness to the peripheral quadrants.

TABLE 2

Corneal-scleral Lenticule Dimensions, Mean (SD), [Range]

| | Thickness (in µm) | | | | | Diameter (in mm) | |
|---|---|---|---|---|---|---|---|
| | Central | Begin of pass | End of pass | Superior | Inferior | Horizontal | Vertical |
| 170 | 294 (37) [258–378] | 249 (64) [151–312] | 293 (49) [214–340] | 299 (31) [265–347] | 318 (39) [287–390] | 12.8 (0.8) [11.8–13.9] | 12.0 (0.6) [11.1–12.7] |
| 200 | 277 (91) [125–428] | 271 (54) [217–365] | 245 (74) [89–329] | 264 (64) [198–409] | 238 (37) [89–349] | 11.9 (0.7) [11.2–12.1] | 11.4 (0.6) [10.8–12.7] |

After Optisol® preservation, the lenticules tended thin. A mean central thickness of 215 $\mu$m (SD 42) was obtained for the 170 blade carriage and 182 $\mu$m (SD 55) for the 200 head. These differences were significant compared to the values obtained immediately after the harvesting procedure (P=0.016 and P=0.031, respectively).

Histology revealed the presence of a multilayer epithelial cell pattern at the lenticule periphery in the limbal area. This may indirectly reflect the presence of intact stem cells in the basal region. The results were similar in both vertical and horizontal meridia. The SEM showed a smooth cut surface in both stromal bed and the lenticule. A transitional zone in the corneal-scleral area was observed, with an evident change of pattern in the orientation of the collagen fibers in the corneal-scleral CS transition zone.

DISCUSSION

The system 10 of this invention produced a reproducible cut in every donor eye. Furthermore, after short term storage in Optisol®, the corneal-scleral CS lamellar lenticules tend to become thinner, making them potentially useful for lamellar corneal transplantation.

The lenticule size was slightly larger in the horizontal meridian using the 170 blade carriage. No differences were observed in the vertical meridian. The smallest vertical diameter of all globes was 10.8 mm in one eye. In the 170 blade carriage group, the smallest diameter obtained was again in the vertical meridian, with 11.1 mm. The means of both groups were significantly above 11.4 mm, which guarantees a size large enough to include the limbus of average eyes.

Histological analysis demonstrated the presence of epithelial cells in the area where limbal stem cells are thought to be present. Although we did not measure the vitality of these cells because of the prolonged post-mortem time of the globes, they appear intact. The thermal-mechanical damage induced by the blade oscillation is negligible. The quality of the dissection was very good up to the edges of the cut.

While this invention has been described with respect to various examples and embodiments, it is to be understood that the invention is not limited thereto and that it can be practiced within the scope of the following claims.

What is claimed is:

1. A method for harvesting from the eye of a mammalian donor a graft which comprises limbal stem cells in addition to corneal tissue, said method comprising the steps of:
   A. providing a graft harvesting device which comprises;
      (i) a ring/guide member that is positionable in contact with the eye, said ring/guide member comprising a ring and a cutting device guide surface; and
      (ii) a cutting device configured to engage the guide surface of the ring/guide member and to move along a path guided by said guide surface;
      (iii) said ring/guide member being sized relative to the eye such that, when the ring member is placed in contact with the eye and the cutting device is engaged with the guide surface and moved along the path guided by said guide surface, the cutting device will remove from the eye a graft that includes limbal stem cells as well as corneal tissue;
   B. placing the ring/guide member in contact with the eye; and
   C. engaging the cutter with the guide surface and moving the cutter on the path guided by the guide surface, thereby removing from the eye a graft that comprises limbal stem cells as well as corneal tissue.

2. A method according to claim 1 wherein the ring/guide member is sized and configured such that the graft removed in Step C comprises corneal tissue and a portion of the sclera wherein limbal stem cells are contained.

3. A method according to claim 1 wherein the graft removed in Step C has limbal stem cells disposed approximately 360 degrees around the corneal tissue.

4. A method according to claim 1 wherein the graft removed in Step C comprises an anterior portion that contains the corneal tissue and limbal stem cells and a posterior lamellar portion that contains an endothelial layer, and wherein the method further comprises the steps of:
   D. separating the anterior portion from the posterior lamellar portion.

5. A method according to claim 4 further comprising the Step of:
   E. storing the posterior lamellar portion for use in endokeratoblasty.

6. A method according to claim 5 wherein Step E comprises trephining the posterior lamellar portion and then storing the trephined posterior lamellar portion for use in endokeratoblasty.

7. A graft comprising corneal tissue and limbal stem cells, said graft having been harvested by a method according to claim 6.

* * * * *